United States Patent
DeWind (10) Patent No.: US 11,340,143 B2
(45) Date of Patent: May 24, 2022

(54) SOIL SAMPLING APPARATUS

(71) Applicant: DeWind One-Pass Trenching, LLC, Zeeland, MI (US)

(72) Inventor: Ryan DeWind, Zeeland, MI (US)

(73) Assignee: One Pass Innovators, LLC, Zeeland, MI (US)

( * ) Notice: Subject to any disclaimer, the term of this patent is extended or adjusted under 35 U.S.C. 154(b) by 319 days.

(21) Appl. No.: 16/458,963

(22) Filed: Jul. 1, 2019

(65) Prior Publication Data

US 2021/0003483 A1 Jan. 7, 2021

(51) Int. Cl.
*G01N 1/12* (2006.01)
*G01N 33/24* (2006.01)
*G01N 1/10* (2006.01)

(52) U.S. Cl.
CPC ............. *G01N 1/12* (2013.01); *G01N 33/24* (2013.01); *G01N 2001/1031* (2013.01)

(58) Field of Classification Search
CPC .............................................. G01N 2001/1031
See application file for complete search history.

(56) References Cited

U.S. PATENT DOCUMENTS

| | | | | | |
|---|---|---|---|---|---|
| 2,287,059 | A * | 6/1942 | Platts | ...................... | E21B 21/16 175/162 |
| 4,112,692 | A * | 9/1978 | Anderson | ............... | E02D 3/054 175/19 |
| 4,166,508 | A * | 9/1979 | Van Den Berg | .......... | E21B 7/20 175/20 |
| 4,332,301 | A * | 6/1982 | Jonell | ....................... | B04C 9/00 175/50 |
| 5,322,133 | A * | 6/1994 | Hart | .......................... | B25D 1/16 175/20 |
| 5,394,949 | A * | 3/1995 | Wright | ..................... | E21B 7/006 175/121 |
| 5,435,399 | A * | 7/1995 | Peterson | ................... | E02D 1/04 175/135 |
| 5,831,185 | A * | 11/1998 | Maxwell | ................. | E21B 7/124 73/864.45 |
| 6,339,966 | B1 * | 1/2002 | Kalidindi | ................. | G01N 1/08 73/864.31 |

FOREIGN PATENT DOCUMENTS

| | | | |
|---|---|---|---|
| CN | 107894346 | * | 4/2018 |
| CN | 108318280 | * | 7/2018 |
| CN | 109030083 | * | 12/2018 |
| JP | 57-110935 | * | 7/1982 |

* cited by examiner

*Primary Examiner* — Daniel S Larkin
(74) *Attorney, Agent, or Firm* — The Watson IP Group, PLC; Jovan N. Jovanovic (57) ABSTRACT

A soil sample collection apparatus is comprised of an extension member, a soil sample collection container, and a collection panel. The extension member includes first and second ends. The soil sample collection container includes first and second ends, the first end of the soil sample collection container being coupled to the second end of the extension member. The collection panel is proximate to the first end of the soil sample collection container, the collection panel moveable to an open position during collection of a soil sample and a closed position during extraction of the soil sample.

14 Claims, 8 Drawing Sheets

SOIL SAMPLING APPARATUS

CROSS-REFERENCE TO RELATED APPLICATION

NA

BACKGROUND OF THE DISCLOSURE

1. Field of the Disclosure

The disclosure relates in general to a sampling apparatus, and more particularly, to a soil sampling apparatus.

2. Background Art

Soil sampling is used for various industrial purposes, with soil sampling taken at various depths. For example, soil sampling provides information related to soil pH, soil composition, fertilization concentration, soil homogenization, etc. Current soil sampling apparatus can take various forms including soil augers that collect soil samples as they are inserted into soil, soil probes that includes a tubular configuration that collect soil sample by friction of soil within this tubular configuration, shovels, scoops, etc.

SUMMARY OF THE DISCLOSURE

The disclosure is directed to a soil sample collection apparatus comprised of an extension member, a soil sample collection container, and a collection panel. The extension member includes first and second ends. The soil sample collection container includes first and second ends, the first end of the soil sample collection container being coupled to the second end of the extension member. The collection panel is proximate to the first end of the soil sample collection container, the collection panel moveable to an open position during collection of a soil sample and a closed position during extraction of the soil sample.

In some configurations, a cross member is coupled to the soil sample collection container proximate to the first end of the soil sample collection container, the cross member securing the collection panel to the soil sample collection container and allowing the collection panel to slide across the soil sample collection container to the open and closed positions during the soil sample collection and extraction, respectively.

In some configurations, the soil sample collection apparatus further comprises a control cable to control movement of the collection panel between the open and closed positions.

In some configurations, the extension member includes an inside surface and an outside surface, and the apparatus further comprises a plurality of guide members coupled to the outside surface of the extension member, with the control cable being disposed within the plurality of guide members and coupled to the collection panel.

In some configurations, a linking member is coupled at one end thereof to the control cable and at another end thereof to the collection panel.

In some configurations, an extraction panel is disposed at the second end of the soil sample collection container, the extraction panel removeable from the soil sample collection container to allow the soil sample to be removed from the soil sample collection container.

In some configurations, the extraction panel includes threads to couple the extraction panel to the soil sample collection container.

In some configurations, the extraction panel includes a plurality of protrusions to assist in removing the extraction panel from the soil sample collection container.

In some configurations, the soil sample collection container includes a square cross section.

In some configurations, the extension member includes a round cross section.

In some configurations, a support cable coupled to the first end of the extension member, the support cable to support the soil sample collection apparatus while the soil sample collection apparatus is moved into position during the collection and extraction of the soil sample.

In some configurations, a soil sample collection system includes the soil sample collection apparatus. The soil sample collection system further comprises an excavator including a hinged boom, wherein the soil sample collection apparatus is coupled to the hinged boom, the hinged boom moving the soil sample collection apparatus into position during the collection and extraction of the soil sample.

In some configurations, the soil sample collection system further comprises a lowering and raising mechanism, coupled to the excavator, to lower and raise the soil sample collection apparatus during collection and extraction, respectively, of the soil sample.

In some configurations, the lowering and raising mechanism includes at least one spool onto which a control cable and a support cable are wound, the control cable being coupled to the collection panel and the support cable being coupled to the extension member.

In some configurations, the at least one spool includes a first spool and a second spool onto which the support cable and the control cable are wound, respectively.

In some configurations, the lowering and raising mechanism further comprises a cable brake, coupled to the excavator, to prevent the control cable from further unwinding from the second spool while the support cable continues to unwind from the first spool.

In some configurations, the lowering and raising mechanism further comprises a cable weight hung from the control cable, the cable weight to prevent tangling of cable slack formed in a cable segment of the control cable.

BRIEF DESCRIPTION OF THE DRAWINGS

The disclosure will now be described with reference to the drawings wherein.

DETAILED DESCRIPTION OF THE DISCLOSURE

While this disclosure is susceptible of embodiment(s) in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

The deficiency with current soil samplers is that when used in excavated trenches, such as when installing a soil-Bentonite wall, the bottom of these trenches may not be an optimal location to take a soil sample. For example, when this excavated trench is used for construction of the soil-based wall that is comprised of existing soil that is mixed with additives from top to bottom and start to finish, the bottom of this trench may not accurately reflect the wall composition. The embodiments disclosed herein overcome such deficiencies associated with current soil sample collection apparatuses.

Figure 1:
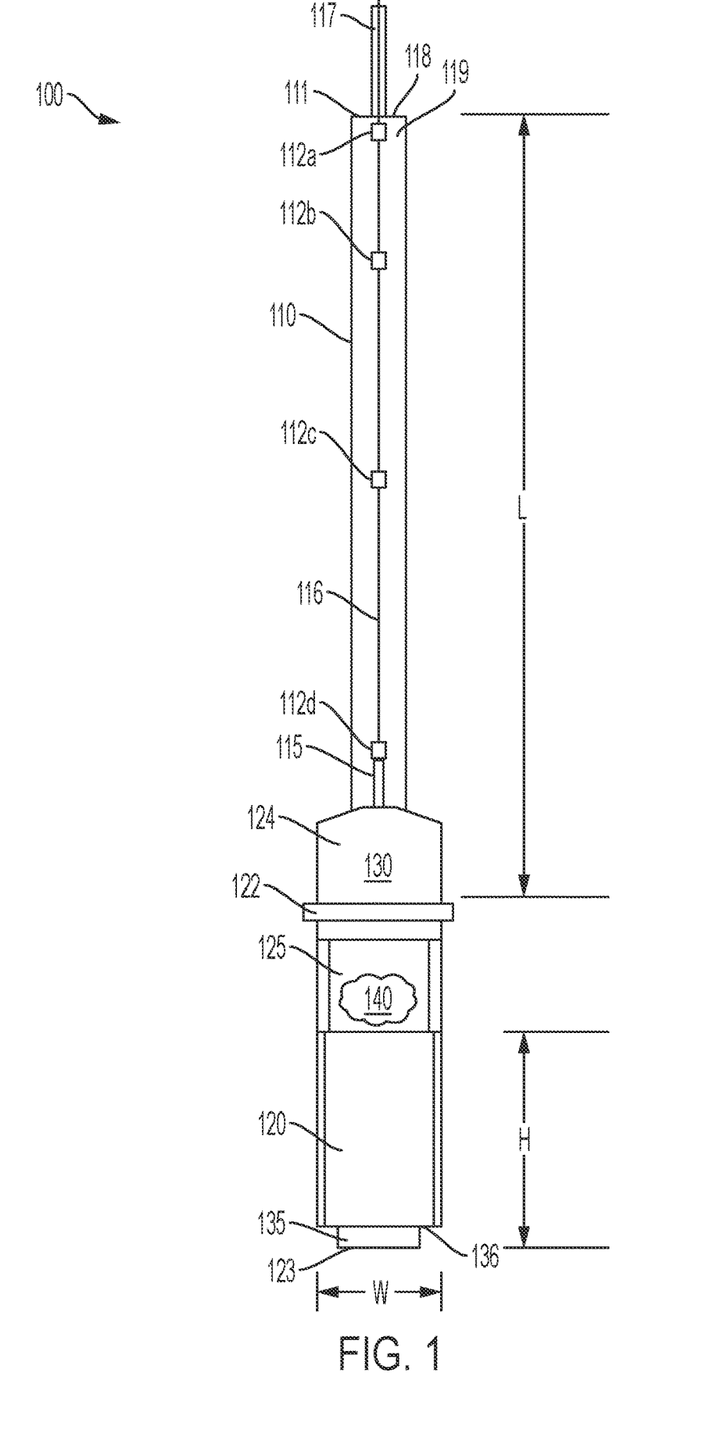
FIG. 1 of the drawings illustrates an example soil sample collection apparatus including a collection panel in an open position of the present disclosure.

Referring now to the drawings and in particular to FIG. 1, an apparatus is disclosed, such as a soil sample collection apparatus 100, including a collection panel 124 in an open position 130 (FIG. 1). FIG. 1 will be described in combination with FIG. 2 that illustrates the soil sample collection apparatus 100 shown in FIG. 1 with the collection panel 124 in a closed position 230 (FIG. 2) and FIG. 3 that illustrates an isometric view of the soil sample collection apparatus 100 shown in FIG. 1 with the collection panel 124 in the open position 130. The soil sample collection apparatus 100 includes an extension member 110 and a soil sample collection container 120. In at least one embodiment, the soil sample collection apparatus 100 is constructed from at least one of steel, aluminum, a non-metal composite material, such as a plastic, or any other material that allows for construction of the soil sample collection apparatus 100.

With the collection panel 124 in the open position 130, an opening 125 is exposed within the soil sample collection container 120 to allow any soil sample 140 within the vicinity of the opening 125 to fall into the soil sample collection container 120. In at least one embodiment, the soil sample collection container 120 has a square cross section, as illustrated. In other embodiments, the soil sample collection container 120 can have other cross sections, such as circular, oval, rectangular, triangular, or another other cross section that allows for collection of a soil sample 140. In at least one embodiment, the extension member 110 has a circular cross section, as illustrated. Likewise, in other embodiments, extension member 110 can have other cross sections, such as circular, oval, rectangular, triangular, or another other cross section that allows for support of the soil sample collection container 120.

The soil sample collection apparatus 100 is comprised of the extension member 110 that includes a first end 111 and a second end 113. The extension member 110 has a length L that can vary depending upon an overall size of the soil sample collection apparatus 100. The length L of the extension member 110 can vary to control how deep the soil sample collection container 120 extends into a soil 425 (FIG. 4) that is proximate to and/or surrounds the soil sample collection container 120 when the soil sample collection apparatus 100 is inserted into this soil 425, to extract the soil sample 140. The extension member 110 further adds weight to the soil sample collection apparatus 100 to assist the soil sample collection apparatus 100 with sinking into a viscous soil when taking the soil sample 140 at large depths, e.g., >20 feet below a soil surface. The extension member 110 can be any width that provides the necessary weight and support for the soil sample collection container 120.

In at least one embodiment, a support cable 117 is coupled to the first end 111 of the extension member 110. This support cable 117 is used to suspend the soil sample collection apparatus 100 in a vertical orientation and support the soil sample collection apparatus 100 while the soil sample collection apparatus 100 is moved into position during collection and extraction of the soil sample 140. In at least one embodiment, the length of the support cable 117 can be varied to extend the soil sample collection container 120 into the soil 425 to extract the soil sample 140. In other embodiments, the soil sample collection apparatus 100 can be supported by a hook, an eye, a rod, or another other mechanism that can suspend the soil sample collection apparatus 100 in a vertical orientation during collection and extraction of the soil sample 140. In at least one embodiment, the support cable 117 is a steel cable or aluminum cable, although in other embodiments the support cable 117 is constructed from other materials.

Figure 2:
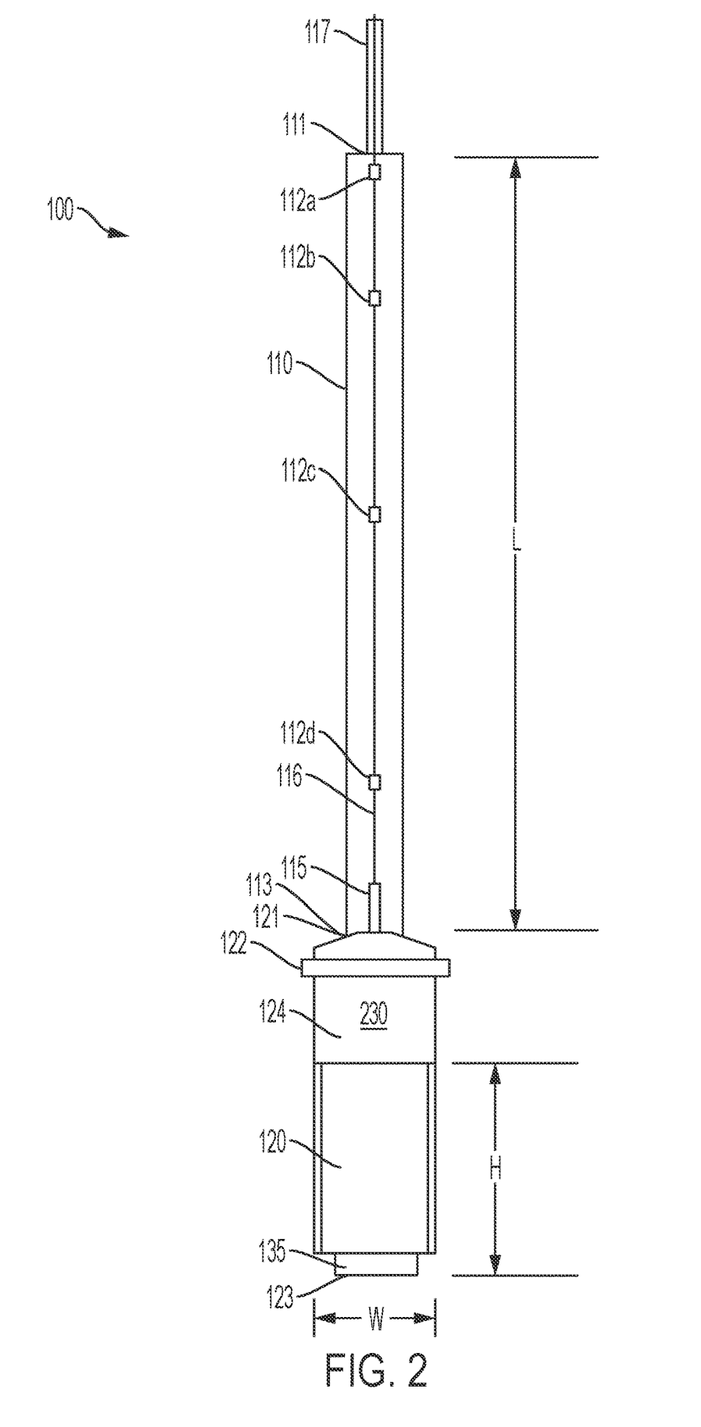
FIG. 2 of the drawings illustrates the soil sample collection apparatus shown in FIG. 1 with the collection panel in a closed position of the present disclosure.

A first end 121 of the soil sample collection container 120 is coupled to the second end 113 of the extension member 110. A collection panel 124 is disposed proximate to the first end 121 of the soil sample collection container 120. The collection panel 124 is moveable to the open position 130 during collection of the soil sample 140 and the closed position 230 during extraction of the soil sample 140 from the soil 425 that the soil sample collection apparatus 100 is inserted into. The collection panel 124 moves to the open position 130 to expose the opening 125 and, as discussed above, allow any soil sample 140 within the vicinity of the opening 125 created by the collection panel 124 moving into the open position 130 to fall into the soil sample collection container 120. In at least one embodiment, the opening 125 is proximate to the first end 121 of the soil sample collection container 120, a height H from the second end 123 of the soil sample collection container 120. This height H allows the soil sample collection apparatus 100 to be dropped into the soil 425 to extract the soil sample 140 a distance, such as height H, from the bottom of a hole or trench, for example when the bottom of the hole or trench is not an optimal location to extract the soil sample 140. This height H can vary depending upon where from the bottom of the hole or trench the soil sample 140 is desired to be extracted.

A cross member 122 secures the collection panel 124 to the soil sample collection container 120. The cross member 122 allows the collection panel 124 to slide across the soil sample collection container 120 to the open position 130 and the closed position 230 during the soil sample collection and extraction, respectively. The cross member 122 is disposed proximate to the first end 121 of the soil sample collection container 120 and in front of the collection panel 124 to secure the collection panel 124 against the soil sample collection container 120. The cross member 122 secures the collection panel 124 against the soil sample collection container 120 in both the open position 130 and the closed position 230 during the soil sample collection and extraction, respectively.

In an embodiment, a control cable 116 is used to control movement of the collection panel 124 between the open position 130 and the closed position 230. In at least one embodiment, a linking member 115 is coupled at one end thereof to the control cable 116 and at the other end thereof to the collection panel 124. The extension member 110 includes an inside surface 118 and an outside surface 119. In at least one embodiment, the soil sample collection apparatus 100 further includes a plurality of guide members 112a, 112b, 112c, 112d coupled to the outside surface 119 of the extension member 110. The plurality of guide members 112a, 112b, 112c, 112d are disposed in approximately a straight line along the length L of the extension member 110. Although four guide members 112 are shown for the extension member 110, more or less guide members 112 can be used depending upon the length L of the extension member 110. For example, a shorter extension member 110 may use less guide members 112, and vise versa. In at least one embodiment, a guide member 112a is disposed proximate to the first end 111 of the extension member 110 and a guide member 112d is disposed proximate to the second end 113 of the extension member 110, with the guide member 112d far enough from the second end 113 of the extension member 110 to allow the collection panel 124 to move upward during the open position 130 of the collection panel 124 without causing interference between the guide member 112d and the linking member 115. The control cable 116 is disposed within the plurality of guide members 112a, 112b, 112c, 112d to move the collection panel 124 moveable between the open position 130 and the closed position 230. In at least one embodiment, the control cable 116 is a steel cable or aluminum cable, although in other embodiments the control cable 116 is constructed from other materials. Although the control cable 116 and the support cable 117 are shown as being cables, one or both can be another force transmitter, such as a chain without departing from the scope of the embodiments. In at least one embodiment, the support cable 117 and the control cable 116 are a same gauge and in other embodiments the support cable 117 and the control cable 116 are different gauges.

Figure 3:
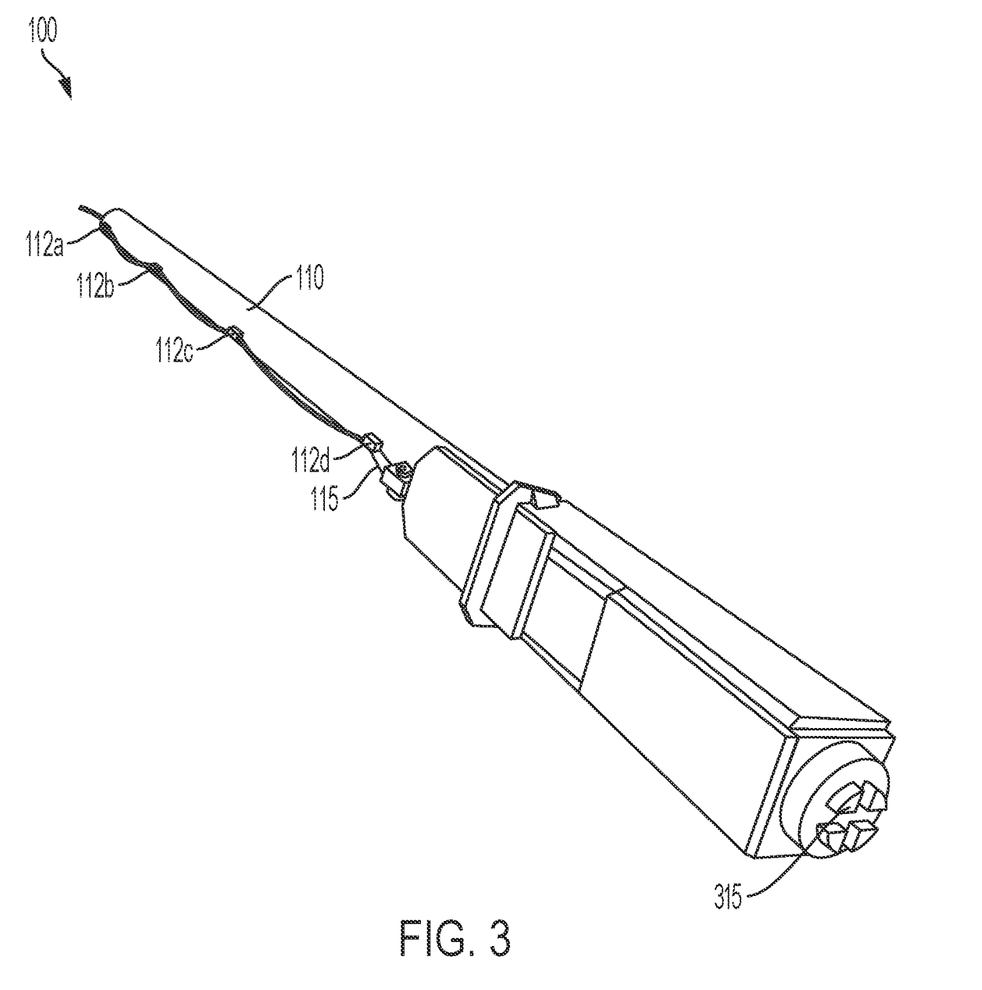
FIG. 3 of the drawings illustrates an isometric view of the soil sample collection apparatus shown in FIG. 1.

In at least one embodiment, the soil sample collection apparatus 100 further includes an extraction panel 135 disposed at the second end 123 of the soil sample collection container 120. The extraction panel 135 is particularly useful to facilitate removal of the soil sample 140 from the soil sample collection apparatus 100 when the soil sample collection apparatus 100 is suspended vertically. In at least one embodiment, the extraction panel 135 includes threads 136 to couple the extraction panel 135 to the soil sample collection container 120. The extraction panel 135 is removeable from the soil sample collection container 120 to allow the soil sample 140 to be removed from the soil sample collection container 120 at the second end 123 of the soil sample collection container 120. In at least one embodiment, the extraction panel 135 screws into the second end 123 of the soil sample collection container 120 via threads 136. In other embodiments, the extraction panel 135 is a hinged door. In at least one embodiment, the extraction panel 135 includes a plurality of protrusions 315 to assist in removing the extraction panel 135 from the soil sample collection container 120, e.g., in screwing the extraction panel 135 off of the soil sample collection container 120. In other embodiments, the extraction panel 135 is a sliding panel, similar to the collection panel 124, to allow the soil sample 140 to be removed from the soil sample collection container 120. In other embodiments, the soil sample collection apparatus 100 does not include the extraction panel 135, with extraction of the soil sample 140 being performed via the collection panel 124.

Figure 4:
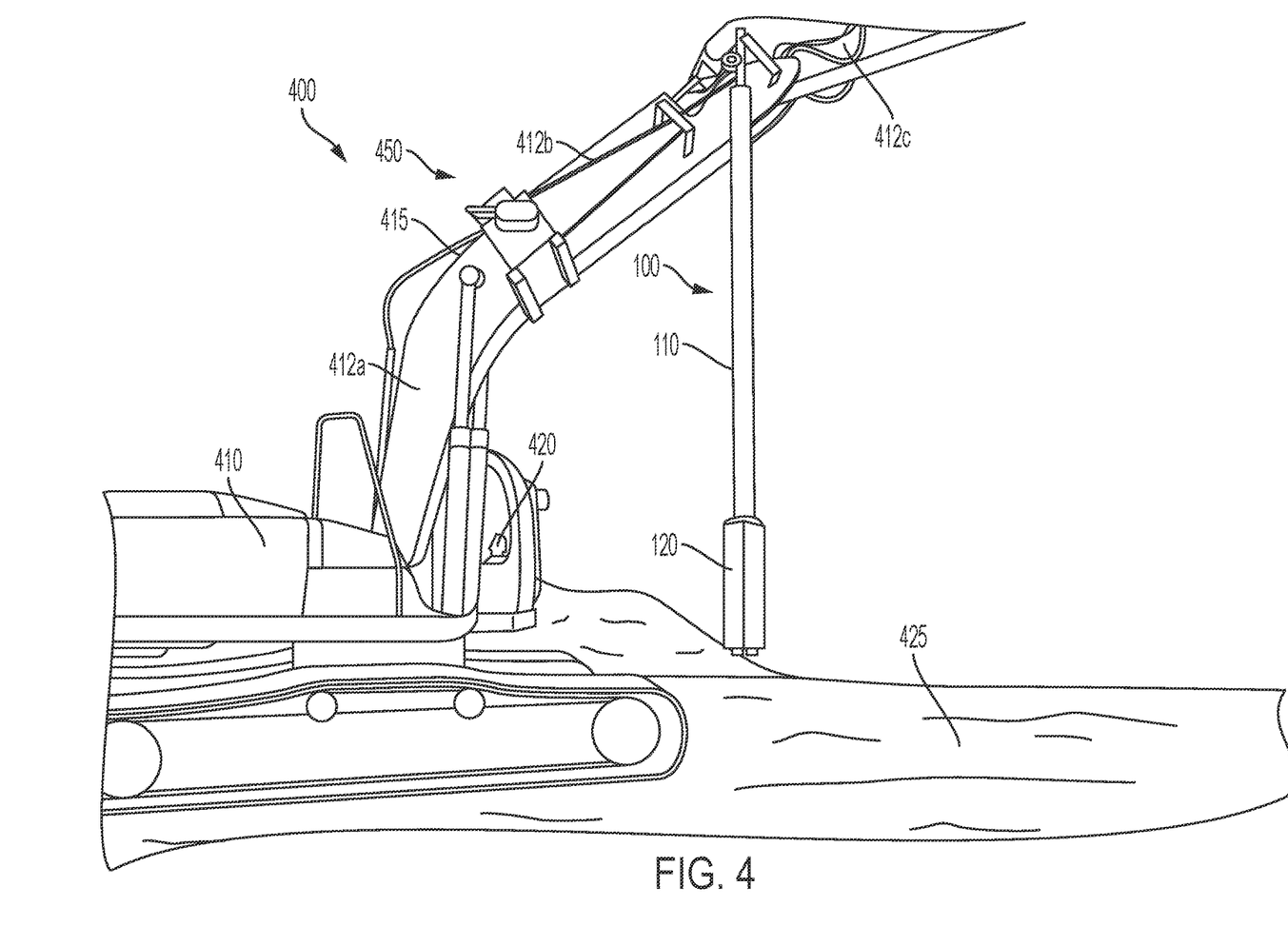
FIG. 4 of the drawings illustrates an example system including the soil sample collection apparatus shown in FIGS. 1-3, coupled to an excavator of the present disclosure.

FIG. 4 illustrates a system, such as a soil sample collection system 400, including the soil sample collection apparatus 100, shown in FIGS. 1-3, and an excavator 410 coupled to the soil sample collection apparatus 100. As shown, a typical excavator 410 includes an excavator hinged boom 415 made up of a plurality of arm segments 412a, 412b, 412c. In at least one embodiment, the soil sample collection apparatus 100 is coupled to the hinged boom 415 via the support cable 117 (FIG. 1). In the example shown, the soil sample collection apparatus 100 is coupled to the hinged boom 415 at a junction between arm segments 412b and 412c, although other locations are possible. However, the soil sample collection apparatus 100 can be coupled to the excavator 410 anywhere along the hinged boom 415.

The hinged boom 415 moves the soil sample collection apparatus 100 into position during the collection and extraction of the soil sample 140. In at least one embodiment, a movement of the control cable 116 to move the collection panel 124 between the open position 130 and the closed position 230 is controlled from the operator's control panel 420. Likewise, in at least one embodiment, the length of the support cable 117 is varied from the operator's control panel 420 to extend the soil sample collection container 120 into the soil 425 proximate the soil sample collection apparatus 100 to extract the soil sample 140.

Figure 5:
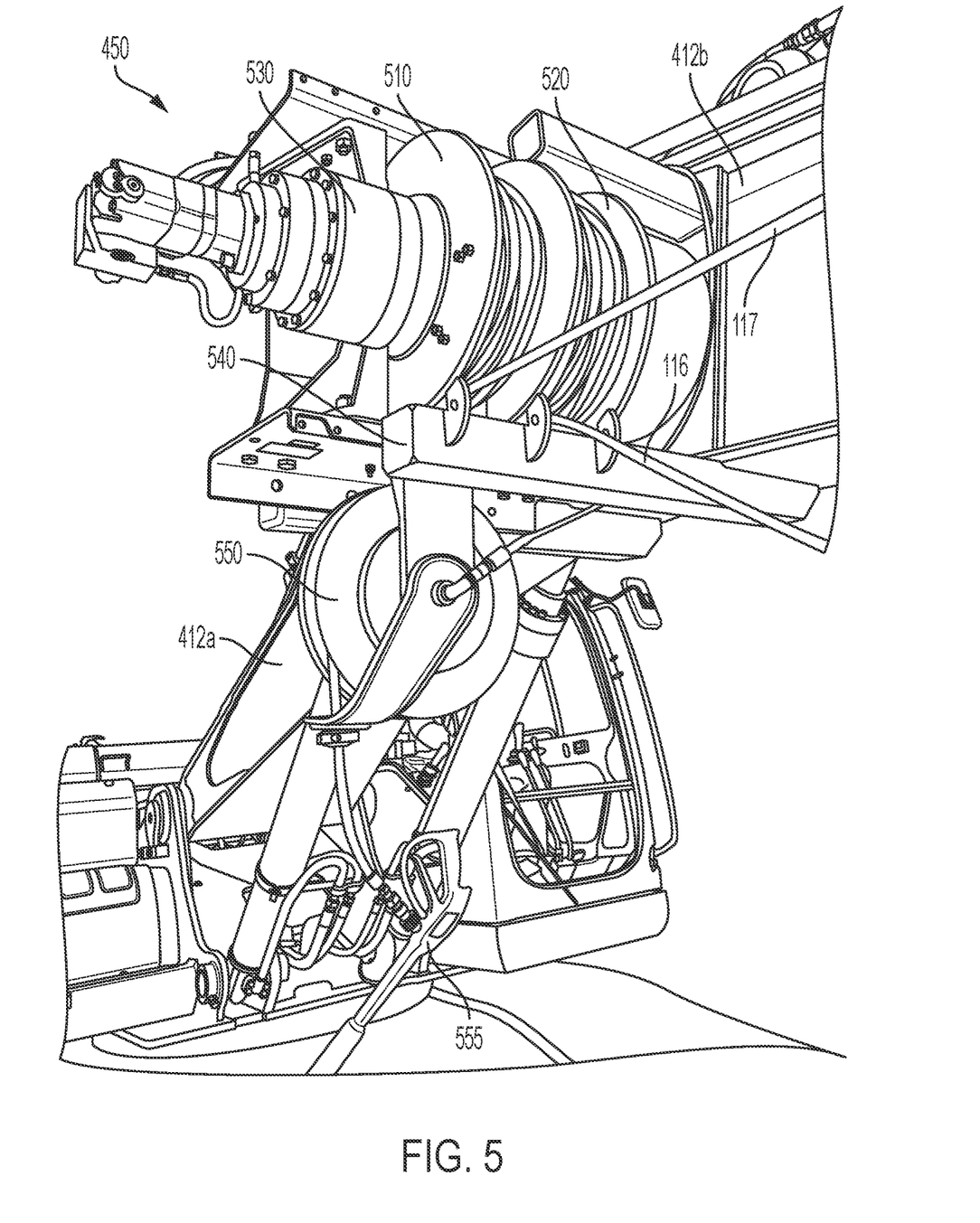
FIG. 5 of the drawings illustrates spools of a lowering and raising system shown in FIG. 4 in greater detail of the present disclosure.
Figure 8:
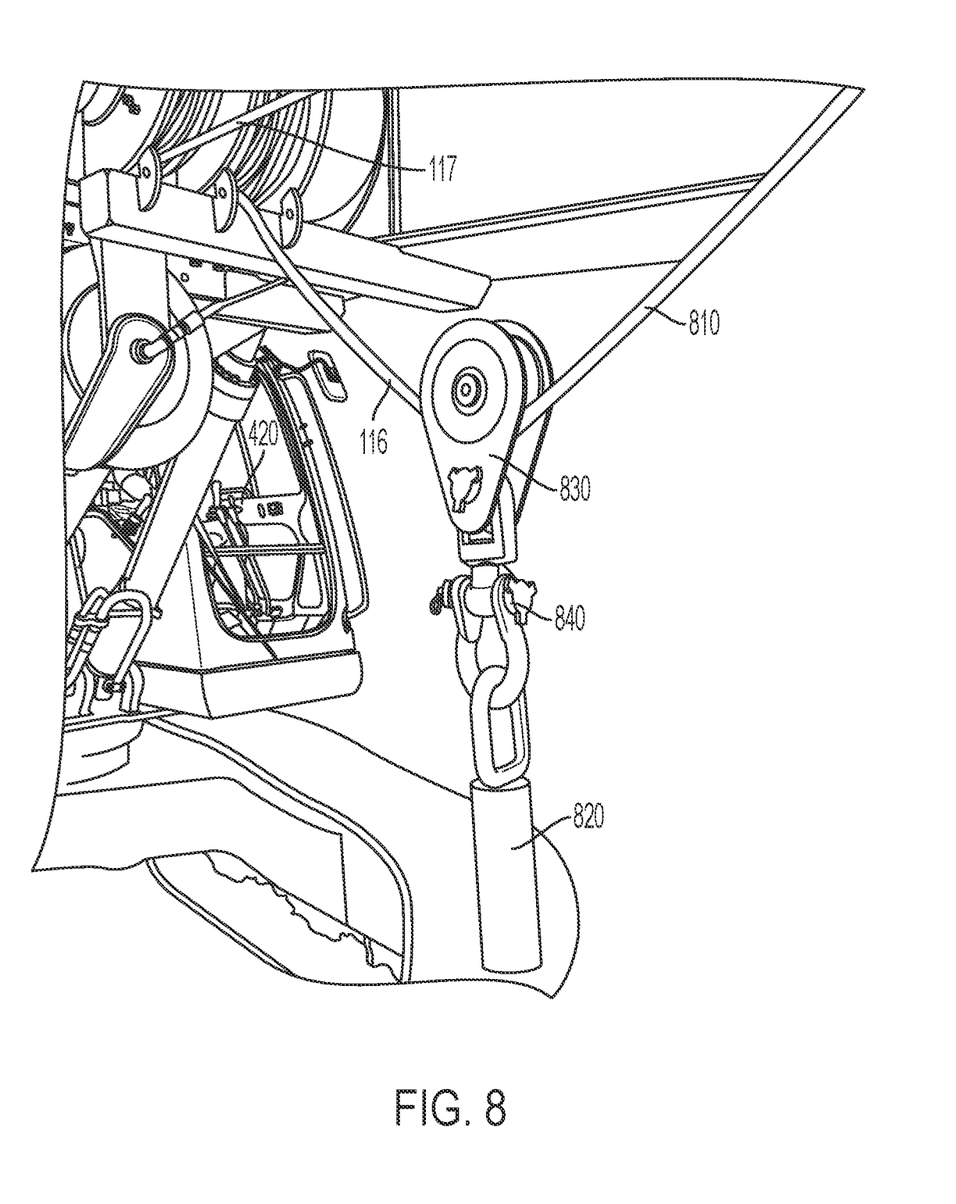
FIG. 8 of the drawings illustrates the lowering and raising system shown in FIG. 4 in greater detail of the present disclosure.

In at least one embodiment, the soil collection system 400 further includes a lowering and raising mechanism 450, coupled to the excavator 410, to lower and raise the soil sample collection apparatus 100 into/from the soil 425 during collection and extraction, respectively, of the soil sample 140. In at least one embodiment, the lowering and raising mechanism 450 includes at least one spool onto which the control cable 116 and the support cable 117 are wound, such as a first spool 510 (FIGS. 5 and 8) and a second spool 520 (FIGS. 5 and 8). For example, the support cable 117 can be wound onto the first spool 510, as shown. Likewise, the control cable 116 can be wound onto the second spool 520, as shown. As shown in FIG. 4 more clearly, the first and second spools 510/520 are coupled to the excavator 410 between arm segments 412a and 412b, although other locations are possible. In at least one embodiment, the first and second spools 510/520 turn in unison as they are both attached to a single motor 530, although in other configurations two motors (not shown) can be used to individually control winding of the control cable 116 and the support cable 117. In at least one embodiment, a housing 540 for the first and second spools 510/520 can serve multiple functions, in the example shown serving as a support for a hose reel 550, such as for a power washing wand 555.

Figure 6:
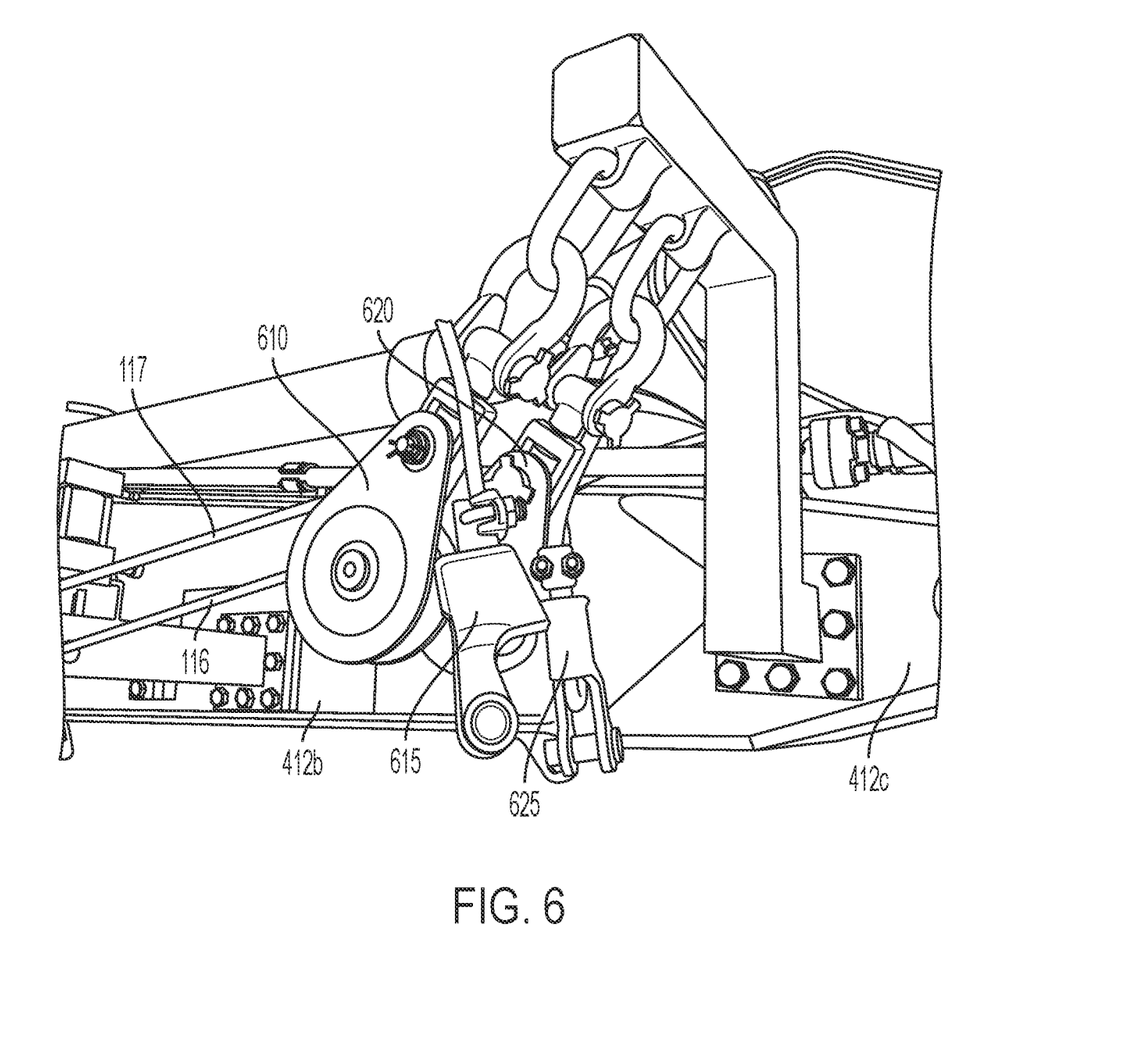
FIG. 6 of the drawings illustrates block and tackles of the lowering and raising system shown in FIG. 4 in greater detail of the present disclosure.

In at least one embodiment, the lowering and raising mechanism 450 further includes a first block and tackle 610 and a second block and tackle 620. For example, the first block and tackle 610 allows a force applied by the motor 530 to be applied to a first coupler 615 and, likewise, the force applied by the motor 530 to be applied to a second coupler 625. The control cable 116 is coupled to the second coupler 625 and the support cable 117 is coupled to the first coupler 615, as shown. In at least one embodiment, the first coupler 615 is coupled to the first end 111 of the extension member 110 and the second coupler 625 is coupled to the control cable 116. As shown in FIG. 4 more clearly, the first and second block and tackles 610/620 are coupled to the excavator 410 where arm segments 412b and 412c couple together, although other locations are possible.

Figure 7:
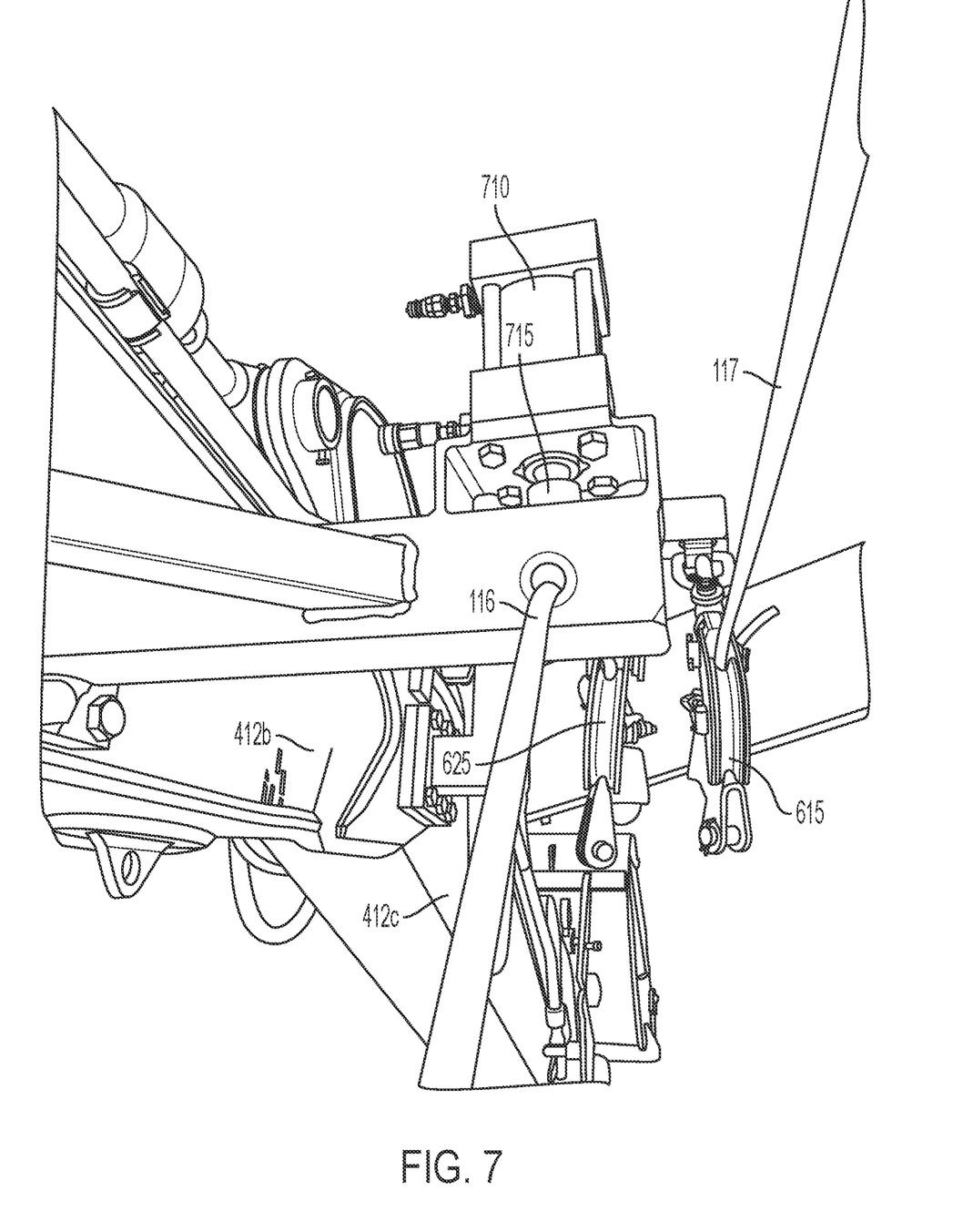
FIG. 7 of the drawings illustrates a cable brake of the lowering and raising system shown in FIG. 4 in greater detail of the present disclosure.

As the control cable 116 and the support cable 117 will unwind from the second spool 520 and the first spool 510 at a same rate unless a mechanism is used to stop one of the cables since both being coupled to the single motor 530, a cable brake 710 (FIG. 7) is used to prevent the control cable 116 from further unwinding from the second spool 520 while the support cable 117 continues to unwind from the first spool 510. The cable brake 710 is coupled to the excavator 410 and includes a piston 715 (e.g., hydraulic piston, pneumatic piston, etc.) that pushes against the control cable 116. With the cable brake 710 activated, such as from the operator's control panel 420, to prevent the control cable 116 from further descent while the support cable 117 is simultaneously allowed to continue descent, an upward force is applied to the collection panel 124 to pull the collection panel 124 into the open position 130. Because the control cable 116 is prevented from further descent while the support cable 117 is simultaneously allowed to continue descent, cable slack will form in a cable segment 810 (FIG. 8) of the control cable 116 disposed before the cable brake 710. A cable weight 820 (FIG. 8) is hung from this cable segment 710, the cable weight 820 pulling down on this cable slack 810 to prevent tangling of this cable slack 810. In at least one embodiment, a third block and tackle 830 (FIG. 8) is utilized to hang the cable weight 820 from the cable segment 810, with a third coupler 840 (FIG. 8) utilized to couple the third block and tackle 830 to the cable weight 820.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. A soil sample collection apparatus, comprising:
   an extension member including first and second ends;
   a soil sample collection container including first and second ends, the first end of the soil sample collection container being coupled to the second end of the extension member;
   a collection panel proximate to the first end of the soil sample collection container, the collection panel moveable to an open position during collection of a soil sample and a closed position during extraction of the soil sample; and
   a cross member coupled to the soil sample collection container proximate to the first end of the soil sample collection container, the cross member securing the collection panel to the soil sample collection container and allowing the collection panel to slide across the soil sample collection container to the open and closed positions during the soil sample collection and extraction, respectively.

2. The soil sample collection apparatus of claim 1, further comprising a control cable to control movement of the collection panel between the open and closed positions.

3. The soil sample collection apparatus of claim 2, further comprising a linking member coupled at one end thereof to the control cable and at another end thereof to the collection panel.

4. The soil sample collection apparatus of claim 1, wherein the soil sample collection container includes a square cross section.

5. The soil sample collection apparatus of claim 1, wherein the extension member includes a round cross section.

6. The soil sample collection apparatus of claim 1, further including a support cable coupled to the first end of the extension member, the support cable to support the soil sample collection container while the soil sample collection container is moved into position during the collection and extraction of the soil sample.

7. A soil sample collection apparatus, comprising:
   an extension member including first and second ends;
   a soil sample collection container including first and second ends, the first end of the soil sample collection container being coupled to the second end of the extension member;
   a collection panel proximate to the first end of the soil sample collection container, the collection panel moveable to an open position during collection of a soil sample and a closed position during extraction of the soil sample; and
   a control cable to control movement of the collection panel between the open and closed positions;
   wherein the extension member includes an inside surface and an outside surface,
   the soil sample collection apparatus further comprising:
   a plurality of guide members coupled to the outside surface of the extension member;
   wherein the control cable is disposed within the plurality of guide members and coupled to the collection panel.

8. A soil sample collection apparatus, comprising:
   an extension member including first and second ends;
   a soil sample collection container including first and second ends, the first end of the soil sample collection container being coupled to the second end of the extension member;
   a collection panel proximate to the first end of the soil sample collection container, the collection panel moveable to an open position during collection of a soil sample and a closed position during extraction of the soil sample; and
   an extraction panel disposed at the second end of the soil sample collection container, the extraction panel removeable from the soil sample collection container to allow the soil sample to be removed from the soil sample collection container.

9. The soil sample collection apparatus of claim 8, wherein the extraction panel includes threads to couple the extraction panel to the soil sample collection container.

10. The soil sample collection apparatus of claim 8, wherein the extraction panel includes a plurality of protrusions to assist in removing the extraction panel from the soil sample collection container.

11. A soil sample collection system including a soil sample collection apparatus, the soil sample collection apparatus comprising:
    an extension member including first and second ends;
    a soil sample collection container including first and second ends, the first end of the soil sample collection container being coupled to the second end of the extension member; and
    a collection panel proximate to the first end of the soil sample collection container, the collection panel moveable to an open position during collection of a soil sample and a closed position during extraction of the soil sample;

the soil sample collection system further comprising:

an excavator including a hinged boom, wherein the soil sample collection apparatus is coupled to the hinged boom, the hinged boom moving the soil sample collection apparatus into position during the collection and extraction of the soil sample; and a lowering and raising mechanism, coupled to the excavator, to lower and raise the soil sample collection apparatus during collection and extraction, respectively, of the soil sample, the lowering and raising mechanism including at least one spool onto which a control cable and a support cable are wound, the control cable being coupled to the collection panel and the support cable being coupled to the extension member.

12. The soil sample collection system according to claim 11, the at least one spool includes a first spool and a second spool onto which the support cable and the control cable are wound, respectively.

13. The soil sample collection system according to claim 12, wherein the lowering and raising mechanism further comprises a cable brake, coupled to the excavator, to prevent the control cable from further unwinding from the second spool while the support cable continues to unwind from the first spool.

14. A soil sample collection system including a soil sample collection apparatus, the soil sample collection apparatus comprising:

an extension member including first and second ends;

a soil sample collection container including first and second ends, the first end of the soil sample collection container being coupled to the second end of the extension member; and a collection panel proximate to the first end of the soil sample collection container, the collection panel moveable to an open position during collection of a soil sample and a closed position during extraction of the soil sample;

the soil sample collection system further comprising:

an excavator including a hinged boom, wherein the soil sample collection apparatus is coupled to the hinged boom, the hinged boom moving the soil sample collection apparatus into position during the collection and extraction of the soil sample; and a lowering and raising mechanism, coupled to the excavator, to lower and raise the soil sample collection apparatus during collection and extraction, respectively, of the soil sample, the lowering and raising mechanism including at least one spool onto which a control cable and a support cable are wound, the control cable being coupled to the collection panel and the support cable being coupled to the extension member, the lowering and raising mechanism further comprising a cable weight hung from the control cable, the cable weight to prevent tangling of cable slack formed in a cable segment of the control cable.

* * * * *